United States Patent [19]

Kamiya et al.

[11] Patent Number: 4,927,222
[45] Date of Patent: May 22, 1990

[54] DUAL OPTICAL FIBER DEVICE

[75] Inventors: Tadao Kamiya, Anaheim; Matthew J. Leader, Long Beach, both of Calif.

[73] Assignee: Shiley Incorporated, Irvine, Calif.

[21] Appl. No.: 874,927

[22] Filed: Jun. 16, 1986

[51] Int. Cl.$^5$ .............................................. G02B 6/26
[52] U.S. Cl. ................................ 350/96.15; 350/96.29
[58] Field of Search ............... 350/96.15, 96.16, 96.23, 350/96.29, 96.34

[56] References Cited

U.S. PATENT DOCUMENTS

| | | | |
|---|---|---|---|
| Re. 31,879 | 0/0000 | Lübbers et al. | 436/133 |
| 4,003,707 | 0/0000 | Lübbers et al. | 23/232 R |
| 4,041,932 | 0/0000 | Fostick | 356/39 |
| 4,200,110 | 0/0000 | Peterson et al. | 356/39 |
| 4,307,933 | 12/1981 | Palmer et al. | 350/96.16 |
| 4,465,335 | 8/1984 | Eppes | 350/96.21 |
| 4,474,431 | 10/1984 | Bricheno | 350/96.15 |
| 4,476,870 | 0/0000 | Peterson et al. | 128/634 |
| 4,548,907 | 0/0000 | Seitz et al. | 436/163 |
| 4,649,271 | 3/1987 | Hök et al. | 350/96.34 X |

FOREIGN PATENT DOCUMENTS

| | | | |
|---|---|---|---|
| 0147168 | 7/1985 | European Pat. Off. | 350/96.16 |
| 3036868 | 5/1982 | Fed. Rep. of Germany | 350/96.15 |
| 53-68249 | 6/1978 | Japan | 350/96.15 |
| 54-13347 | 1/1979 | Japan | 350/96.15 |
| 54-11363 | 8/1979 | Japan | 350/96.15 |

OTHER PUBLICATIONS

George E. Guilbault, "Practical Fluorescence" (1973), pp. 599–600.

Primary Examiner—John D. Lee
Assistant Examiner—Phan Heartney
Attorney, Agent, or Firm—Peter C. Richardson; Lawrence C. Akers; Mark Dryer

[57] ABSTRACT

A device for transmitting electromagnetic radiation to a radiation sensitive component and receiving output radiation from said component comprising a radiation-transmissible junction formed by contacting the tip of a first optical fiber with an intermediate portion of a second optical fiber, said junction being encased in an opaque, radiation reflective jacket. A method for determining a desired parameter using such device is also disclosed.

11 Claims, 1 Drawing Sheet

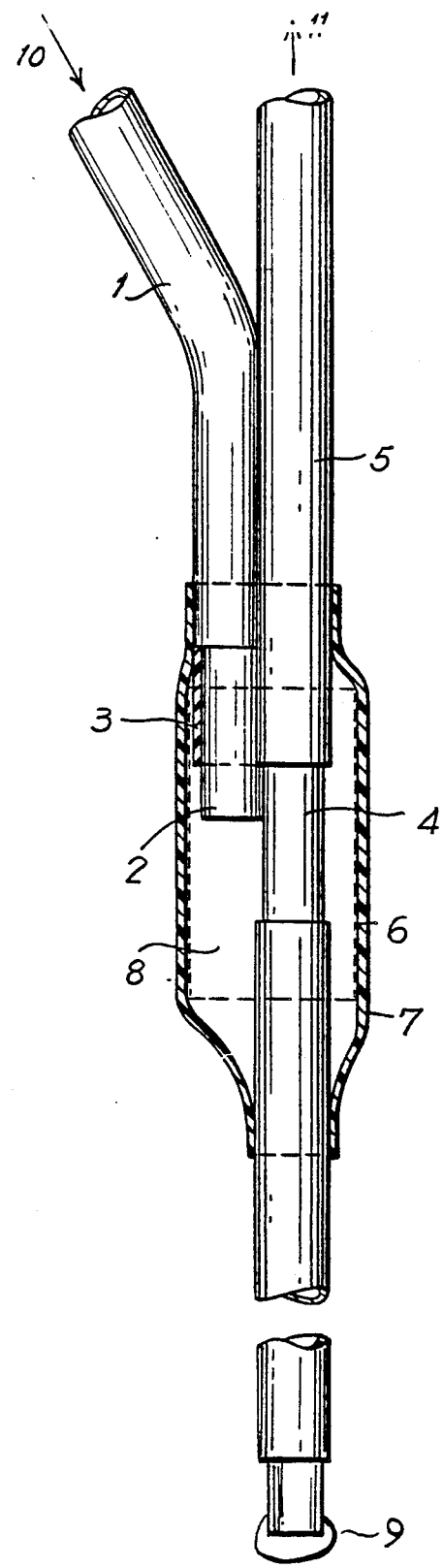

DUAL OPTICAL FIBER DEVICE

BACKGROUND OF INVENTION

This invention relates to a dual optical fiber device and is particularly concerned with a device for transmitting electromagnetic radiation to a radiation sensitive component and receiving output radiation from said component involving a radiation-transmissible junction of optical fibers which provides a substantially unattenuated output radiation signal. The invention also relates to a method for determining a desired parameter which is a function of said output radiation using said device.

The measurement of desired parameters in liquids, particularly in biological systems, is frequently required. For example, the measurement in blood of pH levels and concentration of gases, particularly oxygen and carbon dioxide, is important during surgical procedures, post-operatively, and during hospitalization under intensive care and many devices for the measurement of said physiological parameters have been suggested in the art.

U.S. Pat. No. 4,003,707, Lubbers et al, and its reissue patent Re 31879, disclose a method and an arrangement for measuring the concentration of gases and the pH value of a sample, e.g. blood, involving the use of a fluorescent indicator at the end of a light-conducting cable which is sealingly covered by or embedded in a selectively permeable diffusion membrane. The radiation transmitted to and emitted from the indicator must be passed through various filtering elements and light elements, including reflectors, beam splitters and amplifiers before any meaningful measurements can be made.

U.S. Pat. No. 4,041,932, Fostick, discloses a method whereby blood constituents are monitored by measuring the concentration of gases or fluids collected in an enclosed chamber sealingly attached to a skin "window" formed by removing the stratum corneum over a small area of the patient's skin. The measurements in the enclosed chamber are made, inter alia, by determining the difference in intensity of light emitted from a fluorescent indicator.

U.S. Pat. Nos. 4,200.110 and 4,476,870, Peterson et al, disclose the use of a pH sensitive indicator in conjunction with a fiber optic pH probe. In each of these patents the dye indicator is enclosed within a selectively permeable membrane envelope.

U.S. Pat. No. 4,548,907, Seitz et al, discloses a fluorescent-based optical sensor comprising a membrane immobilized fluorophor secured to one end of a bifurcated fiber optic channel for exposure to the sample to be analyzed.

Many fluorescent indicators sensitive to pH, and thereby useful for $pCO_2$ measurements, are known in the art. Examples of useful fluorescent indicators are disclosed in the above patents and also in "Practical Fluorescence" by George E. Guilbault, (1973) pages 599–600.

Sensor devices using fluorescent indicators may be used for in vitro or in vivo determinations of components in physiological media. For in vitro determinations the size of the device is normally of no consequence, but for in vivo use, the size of the sensor may be extremely critical and there is an increasing need in the art to miniaturize sensor devices, particularly catheter-type devices, for the in vivo determination of components in physiological media, e.g. blood. However, diminution in size of the components of such devices, particularly in the size of the sensor itself, decreases the strength of the signal emitted by the indicator and consequently presents problems in the detection and measurement of said signal. These problems are aggravated when the detector system requires a multiplicity of components, such as filters, beamsplitters and reflectors to isolate and measure the emitted energy. Each of the said components reduces the emitted signal strength resulting in a sequential loss of measurable signal. Consequently, the more components present in the system, the weaker the final signal strength.

It has now been found that the emission signal from radiation-sensitive indicators, particularly fluorescent indicators of the type disclosed in the references discussed above, may be received substantially unattenuated in a suitable detector without the necessity of filters, beam splitters, reflectors or other light elements used in the prior art if the transmitting optical fiber and emission-receiving optical fiber are coupled in a manner according to the present invention, as described hereinafter.

The elimination of the need for additional optical elements provided by the improved device of the present invention allows greater miniaturization of sensor systems than that attainable in prior art systems without loss of signal strength.

SUMMARY OF THE INVENTION

In accordance with the present invention there is provided a device for transmitting electromagnetic radiation to a radiation sensitive component and receiving output radiation from said component in controlled proportions and transmitting said output radiation to a radiation measuring, transducing, recording or retransmitting component, which device comprises a first cladded optical fiber having a proximal end and a distal end, said proximal end being adapted to receive source radiation and said distal end having an exposed tip which substantially contacts an exposed intermediate portion of a second cladded optical fiber having a proximal end and a distal end, the contact between said tip and said second optical fiber forming a radiation-transmissible junction, the proximal end of said second optical fiber being adapted to be attached to a radiation measuring, transducing, recording or retransmitting component and the distal end thereof being attached to a radiation sensitive component, said junction being encased in an opaque, radiation reflective jacket.

The invention also provides a method for determining a desired parameter which is a function of the ouput radiation of a radiation-sensitive component, which comprises transmitting electromagnetic radiation from a source into a device comprising a first cladded optical fiber having a proximal end and a distal end with an exposed tip which substantially contacts an exposed intermediate portion of a second cladded optical fiber having a proximal end and a distal end, said contact forming a radiation-transmissible junction which is encased in an opaque, radiation reflective jacket, said radiation entering the device through the proximal end of said first optical fiber, passing along said first optical fiber and through said junction into said second optical fiber towards the distal end thereof, a major proportion of any radiation not directly passing into said second optical fiber being internally reflected thereinto by the reflective jacket, impinging upon said radiation-sensitive component attached to the distal end of said second optical fiber, causing said component to emit a signal having at least one characteristic dependent upon the parameter to be measured, and said signal passing substantially unattenuated through said second optical fiber toward the proximal end thereof whereby the desired determination is made with the aid of a radiation-detector attached to the proximal end of said second optical fiber.

DETAILED DESCRIPTION OF THE INVENTION

In the device according to the invention the disposition of the second optical fiber with respect to the first optical fiber in said radiation-transmissible junction is such that the output radiation from the radiation sensitive component attached to the distal end of said second optical fiber passes substantially unattenuated along said second optical fiber and through said junction to said measuring, transducing, recording or retransmitting component.

The preferred configuration is that in which the contact between said exposed tip of said first optical fiber and said exposed intermediate portion of said second optical fiber is substantially parallel.

Furthermore, in a preferred embodiment the surface of the exposed tip in contact with the second optical fiber is pre-polished to flatness.

The junction also provides a splitting of the source radiation into two components. A first, minor, component travels to the proximal end of the second optical fiber and the detector and a second, major, component travels to the distal end of the second optical fiber and the radiation-sensitive component. This provides a convenient means for source radiation compensation by measuring the ratio of the first component to the output radiation or emission signal.

The optical fibers used in the device of the invention may be made of any suitable material which will transmit electromagnetic radiation of the desired wavelength. In a preferred embodiment said first and second optical fibers are made of fused silica and the cladding is made of silicone. Fused silica is particularly suitable for the transmission of ultraviolet radiation.

Each of said first optical fiber and said second optical fiber may consist of a single fiber strand or a multiple fiber bundle. Preferably the exposed portion of said second fiber has a length equivalent to at least one fiber diameter.

The opaque, radiation reflective jacket which encases the radiation transmissible junction of the device according to the invention effectively serves two functions; namely, to reflect any radiation which might otherwise escape from the junction back into the second optical fiber and to prevent any extraneous, unwanted radiation from entering the device. Thus, the jacket must be not only internally reflective, but also opaque with respect to external radiation. To accomplish this dual objective it is preferred that said jacket comprises an inner layer and and outer layer, said inner layer being made of a metal foil or a metalized film whose inner surface is coated with a film of reflective material and said outer layer being made of a heat-shrinkable, opaque, non-metallic material.

A preferred metal foil for said inner layer is aluminum foil. A preferred reflective material is barium sulfate.

Also, to enhance the coupling efficiency, it is desirable to apply a layer of optical coupling gel to the film of reflective material.

Said coupling gel is a standard material in the art having substantially the same refractive index as the material of the optical fibers. A typical example is a silicone gel.

The heat-shrinkable, opaque, non-metallic material preferably used as the outer layer of the jacket may be any material which is opaque to ambient radiation and which may be heat shrunk around the junction to form a radiation-tight seal. A suitable material is an opaque plastic, such as polyvinyl chloride. Preferably, to form a completely radiation-tight seal, the outer layer extends over and beyond the inner reflective layer and overlaps the cladded portion of each of the optical fibers.

The device according to the invention is particularly suitable for use in a method for determining a desired parameter which is a function of the output radiation of a radiation-sensitive component. A preferred embodiment of the method is one in which the parameter to be determined is the concentration of a substance in a liquid and said radiation-sensitive component includes a fluorescent indicator whose emission radiation is altered in the presence of said substance.

A typical example of such method is the determination of the concentration of carbon dioxide in blood.

DESCRIPTION OF THE DRAWING

The invention will be more particularly described with reference to a preferred embodiment of the device as illustrated in the accompanying drawing which is a schematic side elevation, partly in section, of said device.

The preferred embodiment illustrated in the drawing comprises a first cladded optical fiber 1 having an exposed tip 2. The fiber is made of fused silica and the cladding 3 is made of radiation-opaque silicone.

The exposed tip of said first optical fiber is in substantially parallel contact with an exposed intermediate portion 4 of a second cladded optical fiber 5 made of the same materials as said first optical fiber.

The contact between said tip and said second optical fiber forms a radiation-transmissible junction which is encased in an opaque, radiation reflective jacket comprising an inner layer made of aluminum foil and illustrated schematically by dashed line 6 and an outer layer 7 made of a heat-shrinkable opaque non-metallic material, for example polyvinyl chloride. The maximum internal diameter of the opaque heat-shrinkable tubing is about 0.01 inch (0.025 mm) when used with a standard fused silica optical fiber of about 400 $\mu$m. diameter. Said outer layer extends beyond the inner metal foil layer and is heat shrunk onto both the inner layer and the cladding of the optical fibers to form a radiation-tight seal around the junction.

The aluminum foil 6 is coated on its inner surface, i.e. the surface facing the junction of the optical fibers, with a film of radiation reflective material, for example barium sulfate. A layer of index matching optical coupling gel, for example silicone gel, is applied to said film of reflective material. This layer substantially fills the space 8 between the reflective layer and the exposed optical fibers.

Attached to the distal end of the second optical fiber (suitably exposed) is a drop of fluorescent indicator 9. Said fluorescent indicator provides a radiation-sensitive component which is excited by radiation 10 entering said first optical fiber from a radiation source (not shown), such as a laser.

In the operation of the device for determining the concentration of a substance in a liquid (not shown) the excitation radiation causes the indicator to fluoresce at a given wavelength. The intensity of the emitted fluorescent radiation is altered by the presence of the substance to be detected and a determination of the concentration of said substance in the liquid under examination may be made by measuring the intensity of the emitted radiation 11 which passes substantially unattenuated through said second fiber to a detector (not shown).

The following Examples illustrate the invention and the manner in which it may be performed.

EXAMPLE 1

This Example illustrates the preparation of a preferred device according to the invention.

The tip of a first silicone cladded 400 μm fused silica optical fiber was stripped of its cladding over a length of about 1 cm. The fiber tip was then polished to flatness with a Buehler fiber optic polisher.

The exposed tip was then washed in acetone to remove residual cladding and polishing grit.

Approximately 1 cm of cladding was stripped from an intermediate portion of a second cladded optical fiber. Removal of the cladding exposed the fused silica fiber. The fiber was washed in acetone to remove residual cladding.

A strip of aluminum foil approximately 6"×6"×0.0045" was cut.

The surface of the foil was then coated with a commercially available white barium sulfate reflectance coating and dried under mild heat.

A small piece, approximately 1"×0.5" of the coated foil was cut from the above dried strip.

A thin layer of optical coupling gel was applied over the reflectance coating.

The polished exposed tip of the first optical fiber was brought into substantially parallel contact with the exposed portion of the second optical fiber. The resulting junction was held in place by taping the cladded portions of the fibers above the junction.

The above prepared foil was rolled into a small cylinder over the barrel of an 18 gauge needle with the light reflective surface on the inside. This cylinder was then slid over the distal end of the second optical fiber and placed over the junction of the two fibers.

A tube of heat-shrinkable white opaque polyvinyl chloride having an internal diameter of about 0.1" (2.54 mm) and a length of about 1" (25.4 mm) was slid over the distal end of the second optical fiber and placed over the reflective foil so that it completely overlapped the ends of the foil. The tube was then exposed to heat until it shrunk down over the foil and thus completely sealed the junction from ambient radiation. An added advantage of the heat-shrinkable outer layer is that it not only secures the fibers in place, but also mechanically strengthens the junction.

EXAMPLE 2

This Example illustrates the use of the device of the invention with an oxygen gas sensor.

A nitrogen gas laser emitting substantially monochromatic radiation having a wavelength of 337 nm. was coupled to the proximal end of the first optical fiber of the device illustrated in Example 1.

A drop of pyrenebutyric acid, a known fluorescent indicator for oxygen, was attached to the distal end of the second optical fiber of the device.

A suitable radiation detector was attached to the proximal end of the second optical fiber of the device and readings were taken for the intensity of emission radiation in the presence of varying concentrations of oxygen gas.

Pyrenebutyric acid, when excited by the above source radiation, emits fluorescent radiation at a wavelength of 396 nm. The intensity of this emitted radiation is quenched in the presence of oxygen and the reduction of the emitted signal gives a determination of the concentration of oxygen.

The results of the test using the device of the invention were as follows:

| Oxygen Concentration ($\chi$ %) | Relative Intensity ($\lambda$ = 396 nm) | Ratio $\frac{\text{Intensity (0\%)}}{\text{Intensity }(\chi\ \%)}$ |
|---|---|---|
| 0 | 137.60 | 1.0 |
| 7 | 94.95 | 1.45 |
| 21 | 62.97 | 2.19 |
| 100 | 21.65 | 6.36 |

The above results show the high signal resolution obtained with the device of the invention and the ability to obtain an accurate quantitative determination of the oxygen concentration.

EXAMPLE 3

This Example illustrates the use of the device of the invention with a carbon dioxide sensor in a liquid medium.

In a similar manner to that followed in Example 2, a nitrogen gas laser emitting substantially monochromatic radiation having a wavelength of 337 nm was coupled to the proximal end of the first optical fiber of the device illustrated in Example 1.

A drop of carboxymethyl umbelliferone, a known pH indicator, was attached to the distal end of the second optical fiber of the device. The indicator was coated with an aqueous gel containing 5 mM sodium bicarbonate and the coated indicator was encased in a carbon dioxide-permeable silicone membrane. The resulting system, when excited by the above source radiation, emits fluorescent radiation at 460 nm and acts as a carbon dioxide sensor.

A suitable radiation detector was attached to the proximal end of the second optical fiber of the device and readings were taken for the intensity of emission radiation in the presence of varying concentrations of carbon dioxide in deionized water.

The results of the test when the sensor was immersed in the deionized water were as follows:

| Carbon Dioxide Concentration ($\chi$ %) | Relative Intensity ($\lambda$ = 460 nm) | Ratio $\frac{\text{Intensity (0\%)}}{\text{Intensity }(\chi\ \%)}$ |
|---|---|---|
| 0 | 99.29 | 1.0 |
| 7 | 83.63 | 1.19 |
| 100 | 45.65 | 2.18 |

As in Example 2, the above results show the high signal resolution obtained with the device of the invention and the ability to obtain an accurate quantitative determination of the concentration of carbon dioxide in a liquid medium.

The device, according to the invention, provides many advantages over prior art optical sensors. Such advantages include:

(1) The use of separate optical fibers for source radiation and output radiation to the detector eliminates the need for dichroic beamsplitters and thus simplifies the radiation measurement system.

(2) The splitting of source excitation radiation at the junction into two components: Component one, the minor component, travelling to the radiation detector, being useful for calibration; and component two, the major component, travelling to the distal end of the second optical fiber for excitation of a fluorescent indicator.

(3) Source compensation of fluorescent measurement by using the ratio of component one of the excitation radiation to the fluorescent emission signal.

(4) Little or no attenuation of emission radiation at the junction, thus maximizing the signal to the detector.

(5) Elimination of additional components as in (1) and substantially no loss of signal strength as in (4) allows optimal miniaturization of the sensor system.

We claim:

1. A device for transmitting electromagnetic radiation to a radiation sensitive component, receiving output radiation from said component and transmitting said output radiation substantially unattenuated to a radiation measuring, transducing, recording or retransmitting component, which device comprises a first cladded optical fiber having a proximal end and a distal end, said proximal end being adapted to receive source radiation and said distal end having a exposed tip which touches but is not integrally joined to an exposed intermediate portion of a second cladded optical fiber having a proximal end and a distal end, the touch contact between said tip and the exposed portion of said second optical fiber forming a highly directional radiation-transmissible junction, the proximal end of said second optical fiber being adapted to be attached to a radiation sensitive component such that the output radiation from said radiation sensitive component passes substantially unattenuated along said second optical fiber and through said junction to said radiation measuring, transducing, recording or retransmitting component, said junction being encased in a opaque, radiation reflective jacket.

2. A device according to claim 1, in which the contact between said exposed tip of said first optical fiber and said exposed intermediate portion of said second optical fiber is substantially parallel.

3. A device according to claim 2, in which the surface of the exposed tip in contact with the second optical fiber is pre-polished to flatness.

4. A device according to claim 1, in which said first and second optical fibers are made of fused silica and the cladding is made of silicone.

5. A device according to claim 1, in which said jacket comprises an inner layer and an outer layer, said inner layer being made of a metal foil or a metalized film whose inner surface is coated with a film of reflective material and said outer layer being made of a heat-shrinkable, opaque, non-metallic material.

6. A device according to claim 5, in which said metal foil is aluminum foil.

7. A device according to claim 5, in which said reflective material is barium sulfate.

8. A device according to claim 5, in which a layer of coupling gel is applied to said film of reflective material, and said layer substantially fills the space between said film of reflective material and the exposed optical fibers.

9. A device according to claim 1, in which said first optical fiber and said second optical fiber each consists of a single fiber strand or a multiple fiber bundle.

10. A method for determining a desired parameter which is a function of the output radiation of a radiation-sensitive component, which comprises transmitting electromagnetic radiation from a source into a device comprising a first cladded optical fiber having a proximal end and a distal end with an exposed tip which substantially contacts an exposed intermediate portion of a second cladded optical fiber having a proximal end and a distal end, said contact forming a radiation-transmissible junction which is encased in an opaque, radiation reflective jacket, said radiation entering the device through the proximal end of said first optical fiber, passing along said first optical fiber and through said junction into said second optical fiber towards the distal end thereof, a major proportion of any radiation not directly passing into said second optical fiber being internally reflected thereinto by the reflective jacket, impinging upon said radiation-sensitive component attached to the distal end of said second optical fiber, causing said component to emit a signal having at least one characteristic dependent upon the parameter to be measured, and said signal passing substantially unattenuated through said second optical fiber toward the proximal end thereof whereby the desired determination is made with the aid of a radiation-detector attached to the proximal end of said second optical fiber.

11. A method according to claim 10, in which the parameter to be determined is the concentration of a substance in a liquid and said radiation-sensitive component includes a fluorescent indicator whose emission radiation is altered in the presence of said substance.

* * * * *